United States Patent
Oh et al.

(10) Patent No.: US 12,145,256 B2
(45) Date of Patent: Nov. 19, 2024

(54) HEALTHCARE ROBOT AND CONTROL METHOD THEREFOR

(71) Applicant: Samsung Electronics Co., Ltd., Suwon-si (KR)

(72) Inventors: Youngjae Oh, Suwon-si (KR); Dongwook Kwon, Suwon-si (KR); Joonho Kim, Suwon-si (KR); Sanghun Lee, Suwon-si (KR); Seongje Cho, Suwon-si (KR); Jonghee Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 478 days.

(21) Appl. No.: 17/288,276

(22) PCT Filed: Nov. 22, 2019

(86) PCT No.: PCT/KR2019/016093
§ 371 (c)(1),
(2) Date: Apr. 23, 2021

(87) PCT Pub. No.: WO2020/141727
PCT Pub. Date: Jul. 9, 2020

(65) Prior Publication Data
US 2021/0394369 A1   Dec. 23, 2021

(30) Foreign Application Priority Data

Dec. 31, 2018  (KR) .................. 10-2018-0173469

(51) Int. Cl.
*B25J 11/00*  (2006.01)
*A61B 5/0205*  (2006.01)
(Continued)

(52) U.S. Cl.
CPC ........... *B25J 11/008* (2013.01); *A61B 5/0205* (2013.01); *B25J 9/161* (2013.01); *B25J 9/1664* (2013.01);
(Continued)

(58) Field of Classification Search
CPC ........ B25J 11/008; B25J 9/161; B25J 9/1664; B25J 9/1679; B25J 11/0005; B25J 19/023; A61B 5/0205
See application file for complete search history.

(56) References Cited

U.S. PATENT DOCUMENTS

2004/0167668 A1    8/2004  Wang et al.
2009/0234499 A1*   9/2009  Nielsen .................... B25J 9/161
                                                    700/250
(Continued)

FOREIGN PATENT DOCUMENTS

JP     2009-509673 A    3/2009
JP        5327668 B2   10/2013
(Continued)

OTHER PUBLICATIONS

Korean Office Action dated Sep. 22, 2023, issued in Korean Application No. 10-2018-0173469.
(Continued)

*Primary Examiner* — Behrang Badii
*Assistant Examiner* — Jay Khandpur
(74) *Attorney, Agent, or Firm* — Jefferson IP Law, LLP

(57) ABSTRACT

A robot is disclosed. The robot comprises: a body including a transport means; a head disposed on the body and including a plurality of sensors; and a processor which controls the head on the basis of at least one sensor among the plurality of sensors and acquires information related to a user's health through the sensor of the controlled head.

10 Claims, 24 Drawing Sheets

(51) Int. Cl.
  *B25J 9/16* (2006.01)
  *B25J 19/02* (2006.01)
(52) U.S. Cl.
  CPC ......... *B25J 9/1679* (2013.01); *B25J 11/0005* (2013.01); *B25J 19/023* (2013.01)

(56) References Cited

U.S. PATENT DOCUMENTS

| | | | | |
|---|---|---|---|---|
| 2012/0197464 | A1* | 8/2012 | Wang | B25J 9/1664 |
| | | | | 701/28 |
| 2015/0094851 | A1* | 4/2015 | Kawabe | G05D 1/0251 |
| | | | | 901/1 |
| 2017/0115755 | A1* | 4/2017 | Jung | A61B 5/0205 |
| 2017/0286651 | A1* | 10/2017 | Erhart | B25J 19/023 |
| 2018/0344215 | A1* | 12/2018 | Ohnemus | A61B 5/1118 |
| 2019/0054626 | A1* | 2/2019 | Ide | B25J 19/026 |
| 2019/0077007 | A1* | 3/2019 | Mallinson | A61B 5/1118 |
| 2019/0118386 | A1* | 4/2019 | Okumura | B25J 13/088 |
| 2019/0366558 | A1* | 12/2019 | Gupta | B25J 11/009 |
| 2020/0205726 | A1* | 7/2020 | Lee | G01S 7/415 |
| 2021/0150145 | A1* | 5/2021 | Negishi | G06V 10/80 |

FOREIGN PATENT DOCUMENTS

| | | |
|---|---|---|
| JP | 2016-165415 A | 9/2016 |
| JP | 2018/175518 A | 11/2018 |
| KR | 10-2006-0084916 A | 7/2006 |
| KR | 10-0820316 B1 | 4/2008 |
| KR | 10-2009-0001723 A | 1/2009 |
| KR | 10-2013-0032891 A | 4/2013 |
| KR | 10-1441285 B1 | 9/2014 |
| KR | 10-2018-0003890 A | 1/2018 |
| WO | 2007/041295 A2 | 4/2007 |

OTHER PUBLICATIONS

Korean Office Action dated May 27, 2024, issued in Korean Application No. 10-2018-0173469.

* cited by examiner

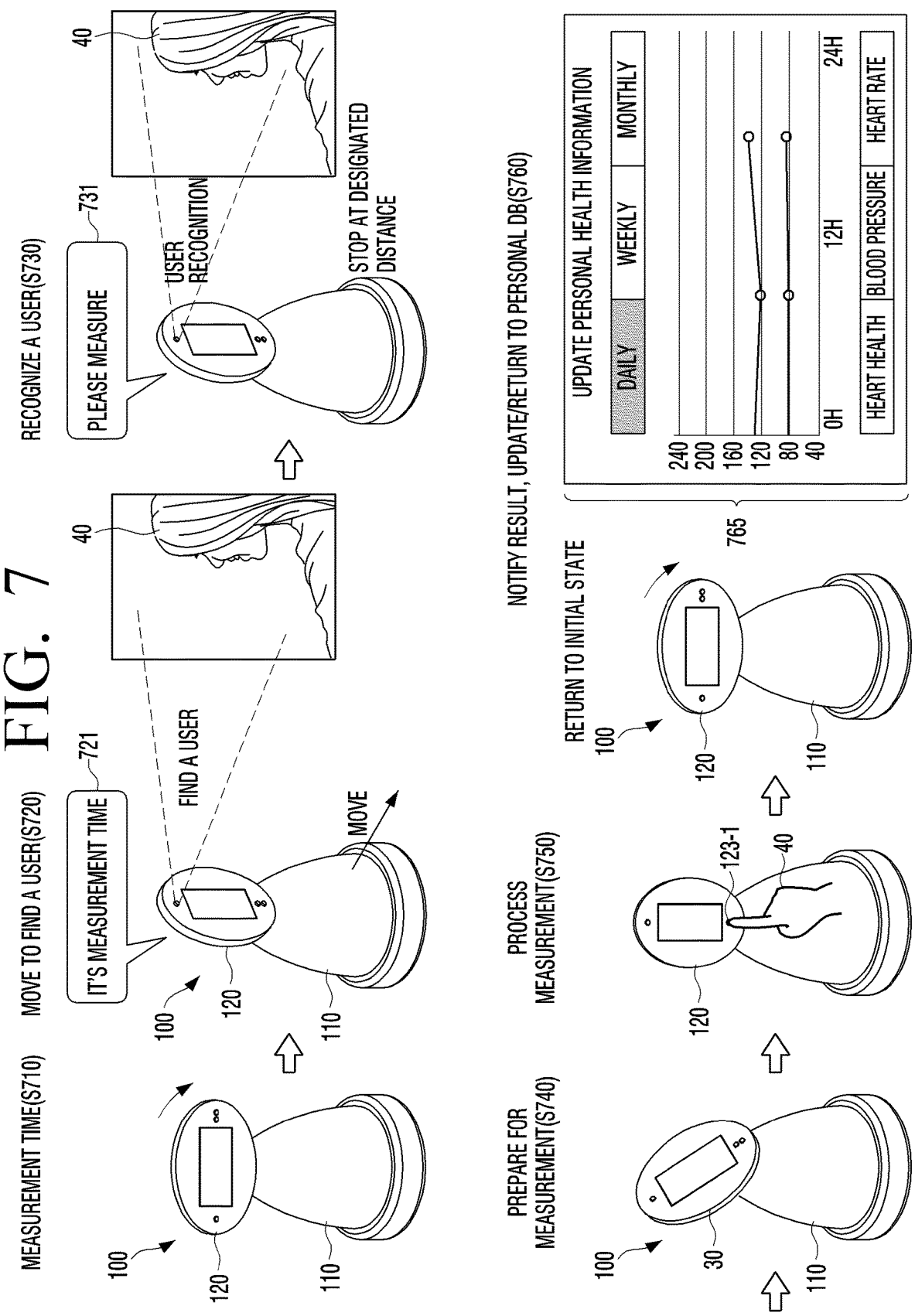

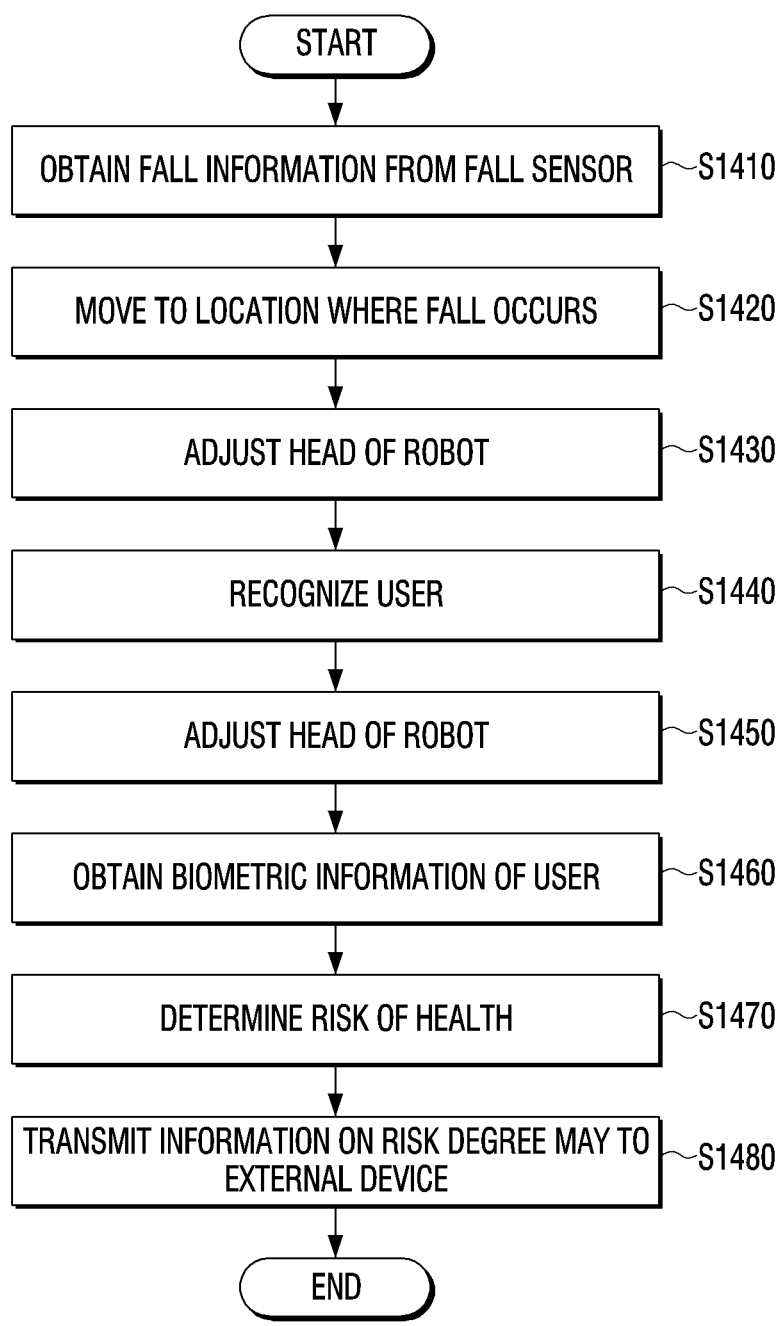

HEALTHCARE ROBOT AND CONTROL METHOD THEREFOR

TECHNICAL FIELD

This disclosure relates to a health care robot. More specifically, the present disclosure relates to a health care robot which is self-moving and changes a posture to obtain various health-related information.

BACKGROUND ART

Various sensing technologies to obtain biometric information have appeared.

A photoplethysmography (PPG) sensor capable of measuring the number of pulses with only a touch, an ultra-wideband (UWB) sensor, which may measure respiration/heart rate without contact with a body, or the like have been developed.

However, since operation principles are different from each sensor, a distance or angle between a user and a sensor for obtaining biometric information from the user may be different for each sensor, and thus each sensor may be implemented as a separate device.

A host of robots that may move autonomously in consideration of peripheral topography and a location of a user have been developed.

DISCLOSURE

Technical Problem

The disclosure provides a health care robot having various sensors which may actively obtain health-related information by autonomously finding a user and moving at each time point using each sensor, to build a database.

The disclosure provides a health care robot which may obtain not only biometric information such as blood pressure or pulse rate but also information on sleep of a user, information on exercise of a user, information on medication of a user, and information on emotion of a user.

The disclosure provides a health care robot which may provide notification for biometric information measurement and provide notification or guide to an operation that a user must perform for health such as exercise or medication.

An objective of the disclosure is to provide a health care robot for providing a comprehensive service related to health management for a user.

Technical Solution

According to an embodiment, a robot includes a body configured to include a moving means, a head that is disposed on the body and includes a plurality of sensors, and a processor configured to adjust the head based on at least one sensor from among the plurality of sensors, and obtain health-related information of a user through the sensor.

The processor may determine a motion angle of the head based on at least one of a location of the sensor or a type of the sensor on the head and adjust the head based on the determined motion angle.

The plurality of sensors may include a camera sensor, and the processor is further configured to determine a posture of the user based on an image obtained through the camera sensor and adjust the head based on the determined posture.

The processor may, based on a time to obtain the health-related information nearing according to preset schedule information, control the body so that the robot approaches a user, and obtain the health-related information using a sensor to obtain health-related information corresponding to the preset schedule information, among the plurality of sensors.

The processor may determine a distance between the robot and the user to obtain the health-related information based on the type of the sensor, and control the body to cause the robot to approach the user based on the determined distance.

The plurality of sensors may include a camera sensor, and the processor may perform authentication for the user using the image obtained through the camera sensor, and update database for the health-related information of the authenticated user based on the obtained health-related information.

The plurality of sensors may include a camera sensor, and the processor may, based on a time for the user to take a medicine nearing according to preset schedule information, obtain an image by capturing the user through the camera sensor, determine whether the user takes medicine based on the obtained image, and update database for the health-related information of the user based on the determined information about whether the user takes medicine.

The robot may further include a display, and the plurality of sensors may include a camera sensor, and the processor may, based on an exercise time of the user nearing based on preset schedule information, display an image to guide the exercise of the user on the display, obtain information about the exercise of the user based on the image obtained through the camera sensor, and display another image to guide the exercise of the user based on the obtained information about the user's motion.

The robot may further include a speaker, and the plurality of sensors may include a camera sensor and a microphone sensor, and the processor may, based on at least one of a voice of the user obtained through the microphone sensor or a face of the user included in an image obtained through the camera sensor, determine an emotional state of the user and reproduce music corresponding to the user's emotional state through the speaker.

The robot may further include a communicator comprising a circuitry, and the processor may, based on receiving information about an emergent situation from an external electronic device through the communicator, control the body so that the robot moves to a location corresponding to the emergent situation based on the received information about the emergent situation, and obtain health-related information of a user present in the location using at least one sensor among the plurality of sensors.

The processor may determine a level of risk of health of the user present in the location based on the obtained health-related information and control the communicator to transmit the obtained health-related information to an external electronic device based on the determined level of risk.

According to an embodiment, a control method of a robot comprising a body including a moving means and a head disposed on the body and including a plurality of sensors includes adjusting the head based on at least one sensor from among the plurality of sensors and obtaining health-related information of a user through the sensor.

The adjusting the head may include determining a motion angle of the head based on at least one of a location of the sensor or a type of the sensor on the head and adjusting the head based on the determined motion angle.

The adjusting the head may include determining a posture of the user based on an image obtained through the camera sensor and adjusting the head based on the determined posture.

The method may further include, based on a time to obtain the health-related information nearing according to preset schedule information, controlling the body so that the robot approaches a user, and the obtaining the health-related information may include obtaining the health-related information using a sensor to obtain health-related information corresponding to the preset schedule information, among the plurality of sensors.

The controlling the body may include determining a distance between the robot and the user to obtain the health-related information based on the type of the sensor, and controlling the body to cause the robot to approach the user based on the determined distance.

The method may further include performing authentication for the user using the image obtained through the camera sensor, among the plurality of sensors, and updating database for the health-related information of the authenticated user based on the obtained health-related information.

The obtaining the health-related information may include based on a time for the user to take a medicine nearing according to preset schedule information, obtaining an image by capturing the user through the camera sensor, determining whether the user takes medicine based on the obtained image, and updating database for the health-related information of the user based on the determined information about whether the user takes medicine.

The method may further include, based on an exercise time of the user nearing based on preset schedule information, displaying an image to guide the exercise of the user on the display, obtaining information about the exercise of the user based on the image obtained through the camera sensor, and displaying another image to guide the exercise of the user on the display based on the obtained information about the user's motion.

The method may include, based on receiving information about an emergent situation from an external electronic device through the communicator, controlling body so that the robot moves to a location corresponding to the emergent situation based on the received information about the emergent situation, and obtaining health-related information of a user present in the location using at least one sensor among the plurality of sensors.

Effect of Invention

The robot according to an embodiment and a control method therefor may have an effect that the robot may move to find a user according to a predetermined schedule or command, and may be automatically transformed into an appropriate posture to obtain health-related information, thereby obtaining various health-related information.

According to the disclosure, the robot and the control method therefor may have an advantage in notifying a user of appropriate information or schedule for health management as a result of obtaining health-related information, and allowing to cope with an emergent situation by notifying the outside, when the user is in a dangerous situation due to a health problem.

DESCRIPTION OF DRAWINGS

FIG. 7 is a diagram illustrating an example of a specific operation order of obtaining health-related information by a robot;

FIG. 14 is a flowchart illustrating a specific embodiment of a case where fall is detected according to a control method of a robot according to an embodiment of the disclosure.

MODE FOR CARRYING OUT THE INVENTION

Figures 1A, 1B:
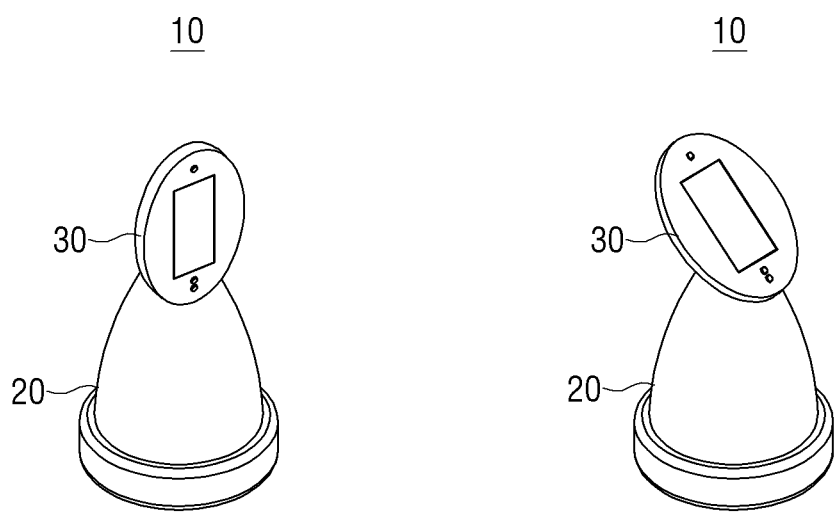
FIGS. 1A and 1B schematically illustrate a physical operation of a robot to obtain information related to health according to an embodiment of the disclosure.

Before describing the disclosure in detail, an overview for understanding the disclosure and drawings will be provided.

The terms used in the present disclosure and the claims are general terms identified in consideration of the functions of the various example embodiments of the disclosure. However, these terms may vary depending on intention, legal or technical interpretation, emergence of new technologies, and the like of those skilled in the related art. Also, some arbitrary terms may be used. Unless there is a specific definition of a term, the term may be understood based on the overall contents and technological common sense of those skilled in the related art.

Further, like reference numerals indicate like components that perform substantially the same functions throughout the disclosure. For convenience of descriptions and understanding, the same reference numerals or symbols are used and described in different example embodiments. In other words, although elements having the same reference numerals are all illustrated in a plurality of drawings, the plurality of drawings do not refer to one embodiment.

The terms such as "first," "second," and so on may be used to describe a variety of elements, but the elements should not be limited by these terms. The terms are used for the purpose of distinguishing one element from another. For example, the elements associated with the ordinal numbers should not be limited in order or order of use by the numbers. If necessary, the ordinal numbers may be replaced with each other.

A singular expression includes a plural expression, unless otherwise specified. It is to be understood that the terms such as "comprise" may, for example, be used to designate a presence of a characteristic, number, step, operation, element, component, or a combination thereof, and not to preclude a presence or a possibility of adding one or more of other characteristics, numbers, steps, operations, elements, components or a combination thereof.

The term such as "module," "unit," "part," and so on may refer, for example, to an element that performs at least one function or operation, and such element may be implemented as hardware or software, or a combination of hardware and software. Further, except for when each of a plurality of "modules," "units," "parts," and the like must be realized in an individual hardware, the components may be integrated in at least one module or chip and be realized in at least one processor executing software.

When any part is connected to another part, this includes a direct connection and an indirect connection through another medium. Further, when a certain part includes a certain element, unless specified to the contrary, another element may be additionally included, rather than precluding another element.

FIGS. 1A and 1B schematically illustrate a physical operation of a robot to obtain information related to health according to an embodiment of the disclosure.

Referring to FIG. 1A, a robot 10 may include a movable body 20 and a head 30 formed on the body.

The robot 10 may move autonomously using a moving means provided in the body 20 (wheels in FIG. 1A), and the head 30 may include a display and various sensors (not shown) for providing information, and the head 30 may be rotated on the body 20 to change the posture as shown in FIG. 1B.

The robot according to the disclosure is a robot capable of physically moving and changing a posture through a body and a head, and the detailed configuration and operation of the robot will be described with reference to the accompanying drawings.

Figure 2:
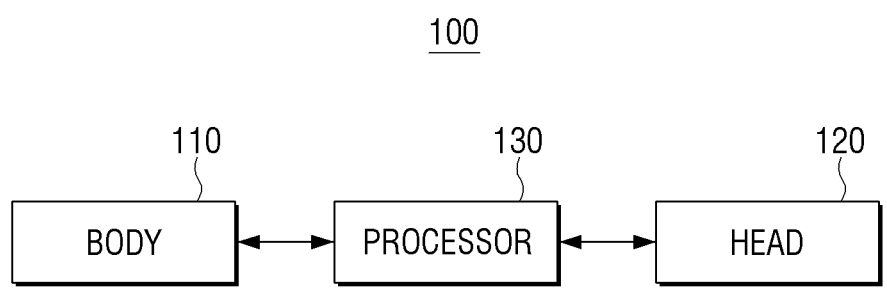
FIG. 2 is a block diagram illustrating a configuration of a robot according to an embodiment of the disclosure.

FIG. 2 is a block diagram illustrating a configuration of the robot 100 according to an embodiment of the disclosure.

Referring to FIG. 2, as described above, the robot 100 may include a body 110, a head 120, and a processor 130.

The body 110 may include a moving means for moving of the robot. The moving means may be in a form of including at least one rotation body such as wheels, but is not limited thereto.

The body 110 may include various sensors such as an air quality sensor (fine dust sensor and/or a gas sensor), an illuminance sensor, a temperature sensor, a distance sensor, a proximity sensor, a radar sensor, a global positioning system (GPS) sensor, an acceleration sensor, or a gyro sensor.

The head 120 may include a plurality of sensors disposed on the body 110. The plurality of sensors may include various sensors for obtaining health-related information such as a photoplethysmography (PPG) sensor, a camera sensor, a microphone sensor, an ultra-wideband (UWB) sensor, an air quality sensor (fine dust sensor and/or a gas sensor), a fall detection sensor, an illuminance sensor, a temperature sensor, a body temperature detection sensor, or the like. The plurality of sensors included in the head 120 may further include various sensors such as a touch sensor, a GPS sensor, an acceleration sensor, and a gyro sensor.

The health-related information may further include various additional information required for health management as well as biometric information such as heart rate (pulse rate), blood pressure, a breathing rate, an eyeball state, voice, skin condition, body temperature, stress degree, emotional state, or the like. For example, information on the exercise of a user, information on a user's medication, information on a user's posture, information on the user's surrounding environment (e.g. air quality, lighting environment, noise, temperature), information on an accident occurrence (e.g., a fall accident of a user), and the like, may be included.

The sensors described as being included in the body 110 or the head 120 may not have to have a fixed location as the body 110 or the head 120, and the location may be implemented otherwise according to a purpose and a place (environment) for the robot 100.

The head 120 may modify the posture on the body 110. For example, the head 120 may be rotated at various angles to take appropriate posture for the sensor to be used among the plurality of sensors. A mechanical structure for adjusting the angle of a head such as a jig/rail may be provided in the body 110, provided on the head 120, or provided across the body 110 and the head 120, but is not limited to the structure of jig/rail.

The processor 130 may control overall operations of the robot 100. The processor 130 may include a random access memory (RAM, not shown), a read only memory (ROM, not shown), a central processing unit (CPU, not shown), a graphic processing unit (GPU, not shown), a system bus (not shown), or the like, and may perform calculation or data processing for control of one or more elements included in the robot 100.

The processor 130 may control one or more elements included in the robot 100, control one or more elements by hardware circuit or chip, or control one or more elements by combination of software and hardware, by executing one or more instructions stored in a memory (not shown).

The processor 130 may be electrically connected to the moving means provided in the body 110, a mechanical structure for rotation of the head 120, or various sensors provided in the body 110 or the head 120 for controlling.

Figure 3A:
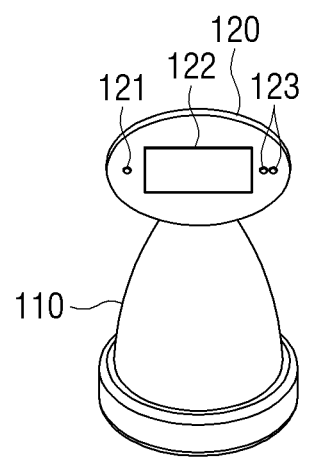
FIG. 3A is a diagram illustrating a configuration of a body and a head according to an embodiment of the disclosure.
Figure 3B:
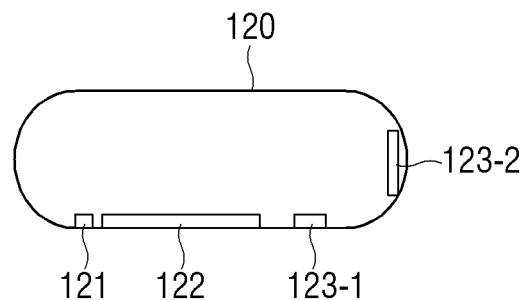
FIG. 3B is a diagram illustrating a configuration of a head in a view from a side surface according to an embodiment of the disclosure.

FIGS. 3A and 3B are diagrams illustrating a configuration of a body and a head according to an embodiment of the disclosure.

Referring to FIG. 3A, the body 110 may include a moving means (not shown, one or more wheels and a center of gravity may be included), and the head 120 may include a camera sensor 121, a display 122, and other sensors 123.

FIG. 3B is a diagram illustrating a configuration of the head 120 in a view from a side surface of the head 120 according to an embodiment of the disclosure.

Referring to FIG. 3B, the camera sensor 121, the display 122, the PPG sensor 123-1, and the like, may be disposed at the front portion of the head 120, the UWB sensor 123-2 may be disposed at a side portion or inside of the head 120, and an angle of the head 120 suitable for using the camera sensor 121 or the PPG sensor 123-1 may be different from an angle of the head 120 suitable for using the UWB sensor 123-2.

While FIG. 3B illustrates only one PPG sensor 123-1 of the other sensors 123 included in the front surface of the head 120 with reference to FIG. 3A, various sensors may be included in the front surface of the head 120. Further, various sensors may be additionally provided on the side portion, rear portion, inner portion and the like of the head 120.

Figure 4A:
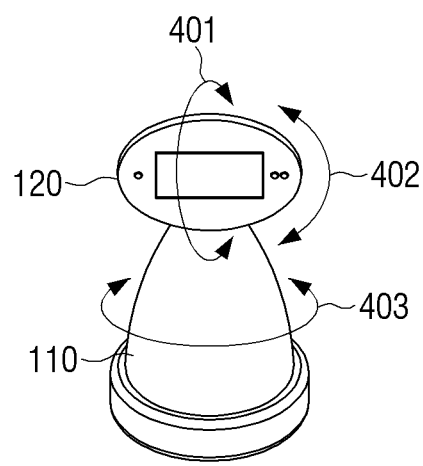
FIG. 4A is a diagram illustrating rotation of a head according to an embodiment of the disclosure.
Figure 4B:
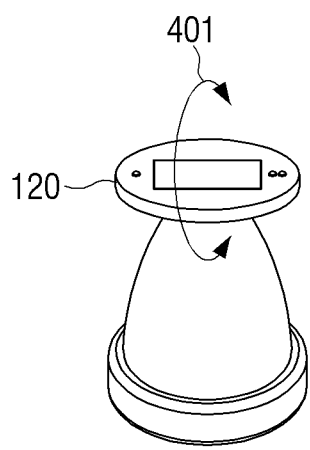
FIG. 4B is a diagram illustrating rotation of a head according to an embodiment of the disclosure.
Figure 4C:
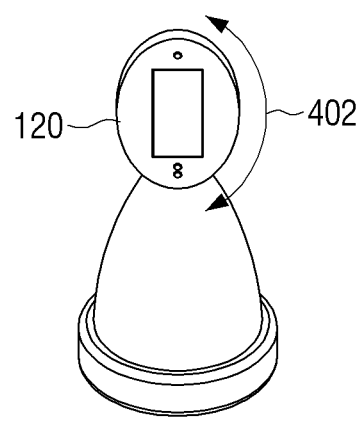
FIG. 4C is a diagram illustrating rotation of a head according to an embodiment of the disclosure.

FIGS. 4A to 4C are diagrams illustrating rotation of a head according to an embodiment of the disclosure.

Referring to FIG. 4A, the head 120 may rotate in direction of 401 so that a direction in which the front portion faces is changed, and/or may rotate in direction 402 while the front portion faces the same direction.

Referring to FIG. 4A, the body 110 itself may rotate in a direction of 403 using the moving means, or a lower region in which the moving means is provided within the body 110 and a separate upper region may rotate in the direction 403 independently of the lower region.

Unlike FIG. 4A, the head 120 may rotate in direction of 403 by itself.

FIG. 4B illustrates that the head 120 of FIG. 4A rotates in direction of 401 so that the front portion of the head 120 faces upward. In this example, the head 120 may return to direction of 402 or 403.

FIG. 4C illustrates a result of the head 120 moving in one direction (clockwise direction) among directions of 402. In the example of FIG. 4B, the head 120 may rotate in the direction of 401.

The rotation direction and angle of the head 120 are not limited to FIGS. 4A to 4C, and the head 120 may rotate in more various directions and angles.

The processor 130 may control the body 110 and the head 120 to obtain health-related information according to predetermined schedule information. The predetermined schedule information may include at least one of the information on the health-related information to be obtained, the time to obtain the health-related information, the target user to obtain the health-related information, or the information on the place to obtain the health-related information.

The information about the health-related information to be obtained may include information about which health-related information may be obtained among various health-related information described above.

For example, the predetermined schedule information may correspond to information on a schedule for measuring a pulse rate of a target user, information on an exercise schedule of the target user (information acquisition for whether a user has exercised through the image obtained through the camera sensor), information on the medication schedule of the target user (information acquisition for whether a user has taken medicine through the image obtained through the camera sensor), or the like. If the predetermined schedule information is information about the exercise or medication schedule, the predetermined schedule information may include information on the type/details/time of the exercise or the type/quantity of the medicine to be taken, together.

The predetermined schedule information may be set according to a user command input through a touch sensor or a microphone sensor provided in the robot 100.

Figure 5A:
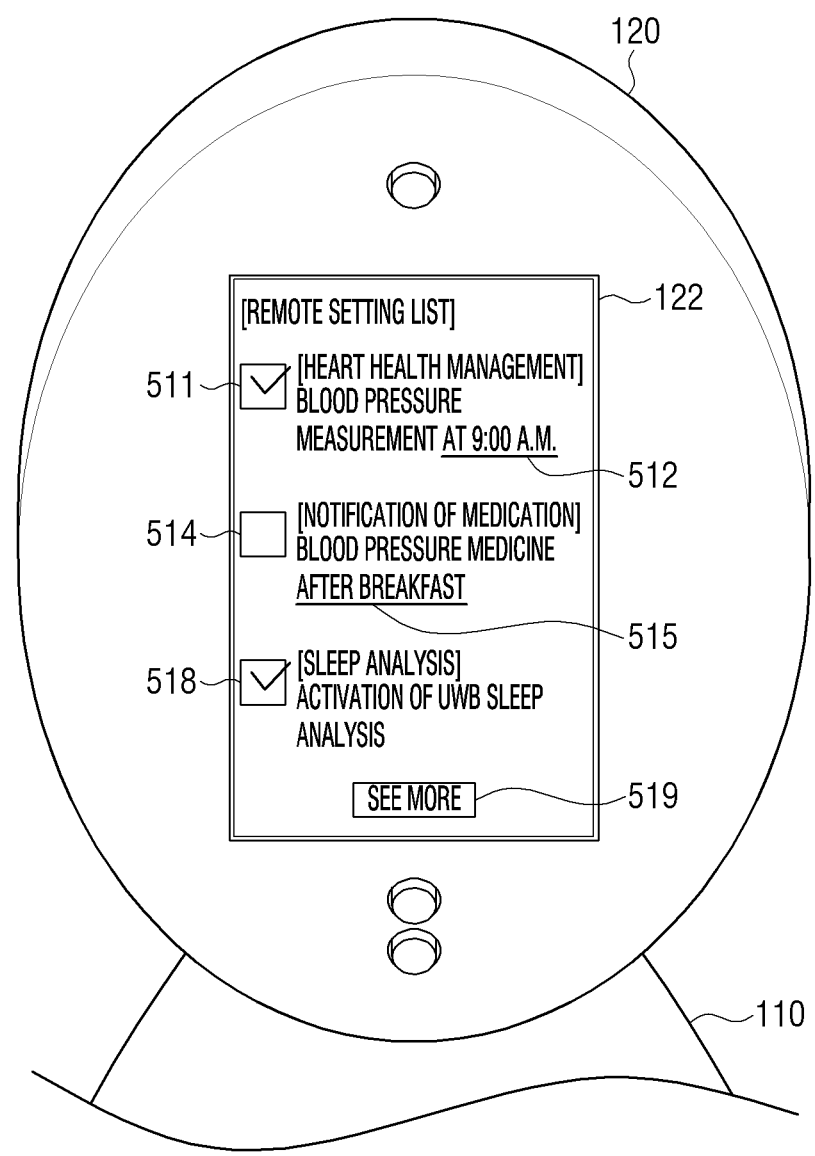
FIG. 5A is a diagram illustrating an example of setting schedule information of a robot.

FIG. 5A illustrates an example in which schedule information is guided and set through the display 122 provided in the head 120 of the robot 100. FIG. 5A assumes a case where a touch pad for receiving a user input is included in the display 122.

Referring to FIG. 5A, the processor 130 may identify that the schedule information to obtain various health-related information is displayed in a form of "health management schedule" through the display 122.

Referring to FIG. 5A, the processor 130 may identify a user's touch for each of the regions 511, 514, and 518, respectively, to generate or remove schedules of "blood pressure measurement for heart health management, "taking a blood pressure medication", and a "sleep analysis", respectively. Referring to regions 511, 514, and 518 of FIG. 5A, the "blood pressure measurement for heart health management" and a "sleep analysis" schedule are generated (activated: checked) currently.

Referring to FIG. 5A, once the user's touch for region 512 or 515 is identified, the processor 130 may control the display 122 to display a graphical user interface (not shown) to change the schedule of "blood pressure measurement" or "taking a blood pressure medicine". The processor 130 may also control the display 122 to display a graphical user interface (not shown) for selecting the type of biometric information to be measured or the type of medicine to be taken.

If the user's touch for "see more" 519 is identified, the processor 130 may control the display 122 to display information for one or more schedules to obtain other health-related information.

As shown in FIG. 5A, the user may set schedule information through the display 122 of the robot 100 as shown in FIG. 5A. However, the embodiment is not limited thereto, and the schedule information may be set by using the user's voice received through the microphone sensor provided in the robot 100.

The preset schedule information may be set according to a user command input through a separate electronic device communicable with the robot 100.

Figure 5B:
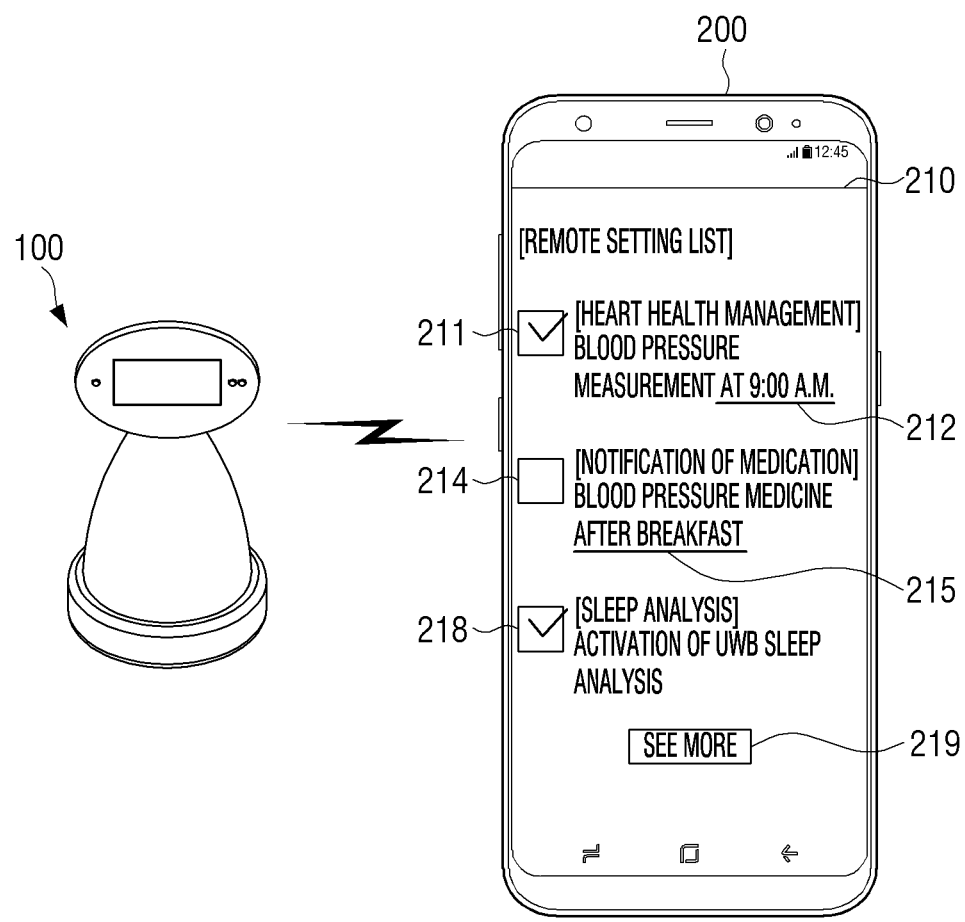
FIG. 5B is a diagram illustrating an example of remotely setting schedule information of a robot using a separate electronic device.

FIG. 5B is a diagram illustrating an example of remotely setting schedule information through a separate electronic device 200. The electronic device 200 may be a mobile phone of a target user obtaining health-related information, but may be a mobile phone of a guardian of the target user, a nurse, a primary doctor, or the like.

FIG. 5B illustrates an example of guiding and setting schedule information through the display 210 of the electronic device 200 which is a communicable mobile phone. FIG. 5B illustrates that a touch pad to receive a user input is included in the display 210.

Referring to FIG. 5B, the schedule information displayed on the display 122 of the robot 100 in FIG. 5A is displayed on the display 210 of the electronic device 200.

The preset schedule information may be set directly through the robot 100, or may be set through the separate electronic device 200 communicable with the robot 100.

The processor 130 may control the body 110 and the head 120 to obtain health-related information according to a user command. The user command may include commands for selecting at least one of the information on the health-related information to be obtained, the time to obtain the health-related information, the target user to obtain the health-related information, or the information on the place to obtain the health-related information. The user command may be directly input through a touch sensor or a microphone sensor provided in the robot 100, or may be input through a separate electronic device and may be received through a communication unit of the robot 100.

For example, the cases may include when a command to measure a pulse of a user is input to the robot 100 with a touch or voice form with respect to the robot 100, or when a control signal corresponding to the pulse measurement command is received from the remote control device receiving the pulse measurement command, etc.

If the time for obtaining the health-related information arrives according to the predetermined schedule information or the user command, the processor 130 may control the body 110 so that the robot 100 may access the target user, and may obtain health-related information of the target user by using a sensor for obtaining health-related information corresponding to predetermined schedule information among the plurality of sensors provided in the robot 100.

However, prior to accessing the target user, the processor 130 may control the body 110 and the head 120 to find the target user to obtain health-related information. Specifically, the location of one or more users may be determined by using a distance sensor, a radar sensor, a microphone sensor, etc. provided in the head 120 or the body 110, and the body 110 may be controlled to move the robot 100 to the identified location.

The processor 130 may identify the location of the target user using the information on the location of the corresponding terminal device received from the terminal device (not shown) of the target user through the communication unit (not shown).

While the robot 100 is moving, the processor 130 may find one or more users by capturing the surroundings of the robot 100 using a camera sensor provided in the head 120. At this time, the angle of the head 120 with respect to one or more directions may be adjusted to capture an image of various angles.

The processor 130 may move to a predetermined place according to a schedule to obtain information about a map of the place where the robot 100 is present and health-related information, and may find the target user.

The processor 130 may obtain a face image of one or more users by using a camera sensor included in the head 120, and perform authentication on whether each user corresponds to a target user by using the corresponding image. At this time, face recognition may be used. Alternatively, the processor 130 may use speech recognition through a microphone sensor (not shown) provided in the head 120 or fingerprint recognition through a separate touch sensor (not shown).

After finding the target user, the processor 130 may determine a distance between the robot 100 and the target user to obtain health-related information based on the type of sensor to be used to obtain health-related information, and may control the body 110 so that the robot 100 may access the target user based on the determined distance.

The processor 130 may control the moving means of the body 110 so as to approach the target user as a distance suitable for obtaining health-related information using the sensor.

The processor 130 may adjust the head 120 based on at least one sensor, among a plurality of sensors provided in the head 120, and may obtain health-related information of the target user using the sensor of the adjusted head.

The processor 130 may determine the motion angle of the head 120 based on at least one of the location of the sensor on the head 120 or the type of the sensor, and may adjust the head 120 based on the determined motion angle. The processor 130 may adjust the posture of the head 120 at an angle suitable for the corresponding sensor to obtain health-related information, depending on the type and/or location of the sensor to be used. The rotation angle of the head 120 relative to one or more directions may be adjusted. In this example, the processor 130 may also take into account the location of the sensor in the head 120 as well as the direction of the sensor.

The type of the sensor may refer to a kind of a sensor. For example, it may be defined that the PPG sensor, the camera sensor, the microphone sensor, the UWB sensor, or the like, may be different types of sensors.

The angle or posture of the head 120 suitable for each of the plurality of sensors may be preset. In this example, the processor 130 may adjust the head 120 in a predetermined angle or posture with respect to the sensor to be used.

The processor 130 may determine the posture of the target user based on the image obtained through one or more camera sensors (not shown) provided in the body 110 or the head 120, and adjust the head 120 based on the determined posture. Although the processor 130 uses the same sensor, the processor 130 may adjust the angle of the head 120 differently according to the posture of the user.

The processor 130 may update a database for health-related information of the target user based on the obtained health-related information. After obtaining health-related information for an authenticated target user, a database for health-related information of the user may be updated.

As an example, information on whether the user's medication is taken, information on the exercise of the user, biometric information of the user, and the like may be obtained, and a database for health-related information of the corresponding user may be updated by using the information.

The database for health-related information may be stored in a memory (not shown) of the robot 100 or stored in a separate external device (not shown). If a database for health-related information is stored in an external device, the processor 130 may transmit the obtained health-related information to an external device through a communication unit (not shown).

The processor 130 may control the display and/or audio outputter to provide information included in database for information related to health of each user according to a user's command or a preset cycle.

The processor 130 may perform authentication prior to providing information included in the database for health-related information of each user. For example, when a command to read a database for health-related information of a particular user is input, the processor 130 may perform face recognition through an image obtained through the camera sensor and provide corresponding information only to a corresponding user or a guardian of the corresponding user. In providing information included in the database for health-related information of each user, the processor 130 may use various authentication such as fingerprint authentication, authentication using voice recognition, password authentication, etc., in addition to authentication using face recognition.

Referring to FIGS. 6A to 6F, for example, the robot may obtain various health-related information by using one or more sensors.

Figure 6A:
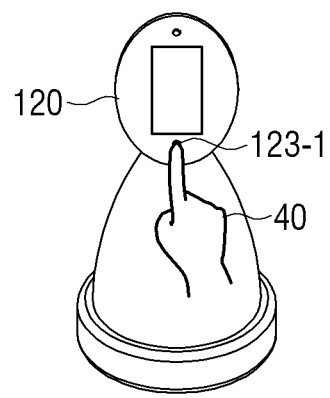
FIG. 6A is a diagram illustrating an example of an operation to obtain health-related information.

FIG. 6A is a diagram illustrating an operation of obtaining a user's pulse rate (heart rate) using the PPG sensor 123-1. FIG. 6A shows that the user 40 may measure the pulse rate of the user 40 by only contacting one of the fingers to the PPG sensor 123-1 of the robot.

Prior to the situation of FIG. 6A, the processor 130 may find the user 40 to be measured using a camera sensor provided in the head 120. Here, authentication may be performed for one or more users regarding the user 40 is a target to be measured. In this case, the processor 130 may adjust the angle of the head 120 to easily capture the face of one or more users through the camera sensor.

Referring to FIG. 6A, the processor 130, which searches for the user 40 successfully authenticated, may control the body 110 to approach the user 40 to be measured. The processor 130 may measure the pulse rate of the user using the PPG sensor 123-1.

Referring to FIG. 6A, since the PPG sensor 123-1 is disposed at the front portion of the robot, the processor 130 may adjust the angle of the head 120 such that the front portion of the head 120 faces the user or slightly above the user so that the user 40 may easily touch the PPG sensor 123-1 with a finger.

While not shown in FIG. 6A, the processor 130 may provide guidance to the PPG sensor 123-1 to touch the finger visually and/or audibly through the display 122 and/or audio outputter (not shown). Further, the processor 130 may provide information on the measured pulse rate through the display 122 and/or audio outputter (not shown).

The processor 130 may determine a degree of stress, blood pressure, or the like, by re-processing the information about the pulse rate, or the like, obtained through the PPG sensor 123-1 using the preset algorithm.

Figure 6B:
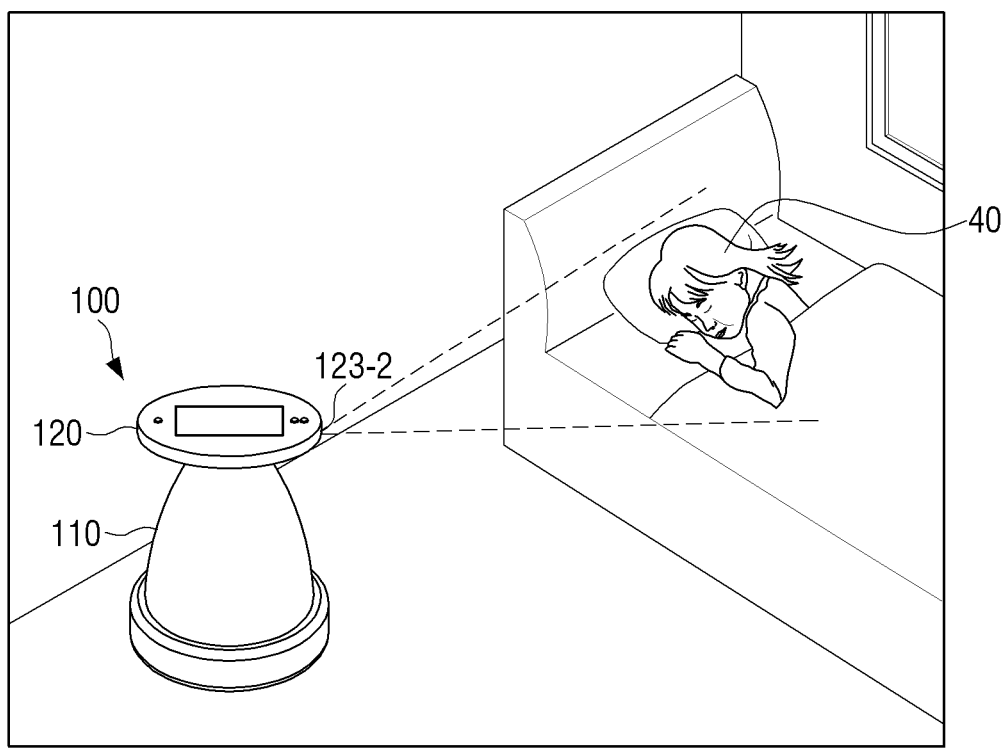
FIG. 6B is a diagram illustrating an example of an operation to obtain health-related information.

FIG. 6B illustrates an example in which the robot 100 obtains information on the quality of sleep such as a breathing rate/heart rate of a sleeping user 40 by using a UWB sensor disposed on a side surface of the head 120.

Prior to the situation of FIG. 6B, the processor 130 may find the user 40 to be measured, using a camera sensor provided in the head 120 or the body 110. At this time, the user may perform authentication for one or more users whether the one or more users are to be measured. The processor 130 may adjust the movement of the body 110 and the posture (angle) of the head 120 to easily capture the face of one or more users through the camera sensor.

When the authentication is successful, and the user 40 to be measured is found, according to the posture of the user 40 who is sleeping, the body 110 may be controlled to move to a location at which information about the breathing rate/heart rate may be easily obtained using the UWB sensor.

As shown in FIG. 6B, the processor 130 may adjust the angle of the head 120 so that the UWB sensor disposed on the side surface of the head 120 faces the user 40, and then may obtain health-related information of the user 40 through the UWB sensor. The processor 130 may further obtain information about the posture of the user 40 during sleep by using the camera sensor.

The processor 130 may control the robot 100 in a mode to minimize an action of another configuration in the robot 100 other than the UWB sensor (and camera sensor) or to minimize a noise by reducing calculation of each configuration or amount of actions, or the like.

The processor 130 may control the display or the audio outputter to provide information on the quality of sleep such as information on a breathing rate/heart rate and/or information on posture during sleeping of the obtained sleep of the user 40, in the morning when the user 40 wakes up.

Figure 6C:
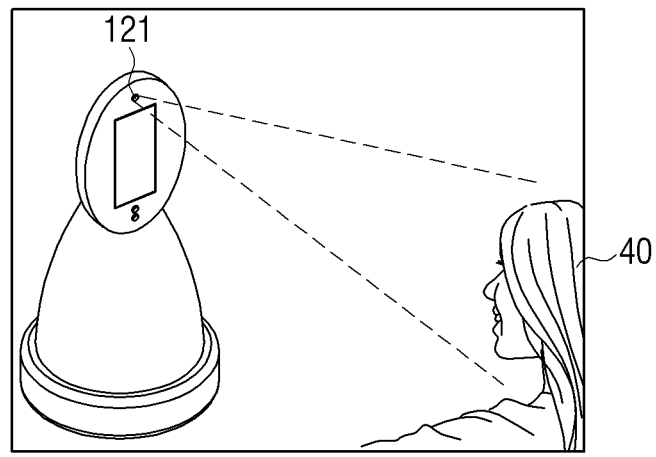
FIG. 6C is a diagram illustrating an example of an operation to obtain health-related information.

FIG. 6C illustrates an example of obtaining information about pulse rate (heart rate) of a user by using the camera sensor 121 included in the head 120 by the robot 100.

Referring to FIG. 6C, the processor 130 may determine the position and/or posture of the user 40 using the image obtained through the camera sensor included in the body 110 or the head 120, and may control the body 110 to move to a location that is easy to obtain an image of the face of the user 40 using the camera sensor 121 according to the determined location and/or posture.

The processor 130 may identify a change in color of the surface of the face and may detect the heart rate by analyzing at least one attribute among red, blue, and green of the obtained face image.

While not shown in FIG. 6C, the processor 130 may provide guidance to watch the camera sensor 121 visually and/or audibly through the display 122 and/or audio outputter (not shown). Further, information on the measured pulse rate may be provided via display 122 and/or audio outputter (not shown).

Figure 6D:
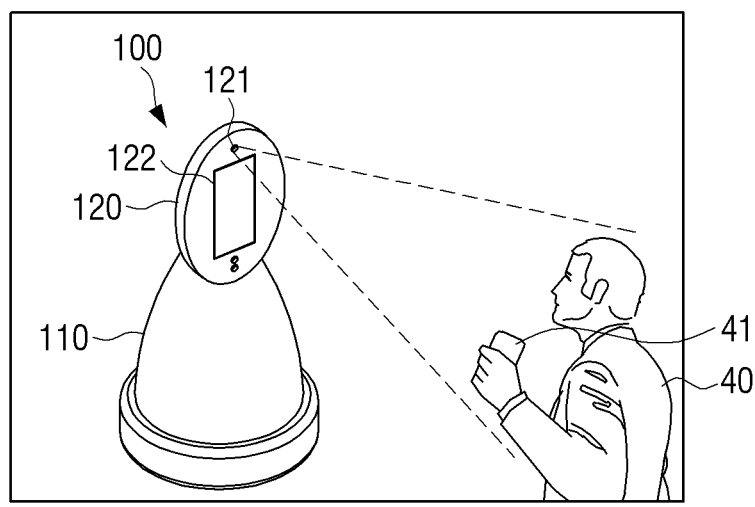
FIG. 6D is a diagram illustrating an example of an operation to obtain health-related information.

FIG. 6D illustrates an example of obtaining information about medication of a user using a camera sensory by the robot 100.

Prior to obtaining information about medication, the processor 130 may control the body 110 so that the robot 100 approaches the user or control the display/audio outputter of the body 110 or the head 120 to inform guidance about medication visually/audibly. Specifically, guidance including information on the type of medication to take, quantity, and administration method of the medicine visually/audibly.

The processor 130 may obtain an image by capturing the corresponding user through the camera sensor when the time at which the user needs to take medicine according to predetermined schedule information, and determine whether the corresponding user is taken based on the obtained image. In this case, an artificial intelligence model trained to output information on the behavior of a user may be used by analyzing the behavior of the user included in the input image.

For example, referring to FIG. 6D, the processor 130 may determine whether the user 4 takes a medicine 41 corresponding to the preset schedule, as a result of analyzing an image obtained through the camera sensor 121.

The database for health-related information of the user 40 may be updated on the basis of the determined information on whether the medication is taken. Specifically, the user 40 may update the database using information about which and how much medicine the user 40 takes, or the like.

Figure 6E:
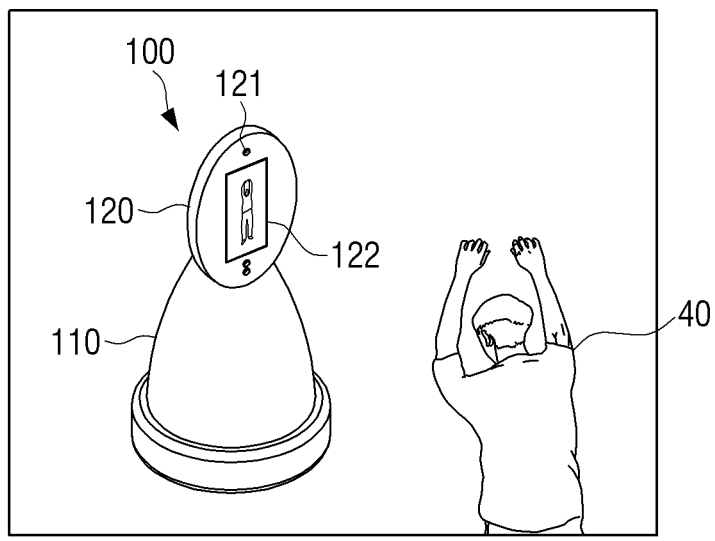
FIG. 6E is a diagram illustrating an example of an operation to obtain health-related information.

FIG. 6E is a diagram illustrating an example of obtaining information about exercise of a user using a camera sensor by the robot 100.

Prior to obtaining information about the exercise of the user, the processor 130 may control the body 110 to approach the user and may visually or audibly notify that the exercise time nears, through the display or the audio outputter.

The processor 130 may display an image for guiding the exercise of the user on the display when the exercise time of the user nears according to the predetermined schedule information, and may obtain information on the exercise of the user based on the image obtained through the camera sensor. In this example, an artificial intelligence model trained to output information on the behavior of a user may be used by analyzing the behavior of the user included in the input image.

For example, referring to FIG. 6E, the processor 130 may display an image for describing the exercise posture of the type corresponding to the predetermined schedule information on the display 122. Referring to FIG. 6E, the processor 130 may capture an image of the user 40 using the camera sensor 121. The processor 130 may provide a message such as "please follow the posture in the photo (video) which I show you" visually or audibly through the display 122 or the audio outputter.

The processor 130 may obtain information about the exercise of the user using the captured image. To be specific, the processor 130 may identify how long the user takes which posture and which motions of exercise.

The processor 130 may also display another image for guiding exercise of the user based on the obtained information on the user's exercise. For example, if the user 40 follows the exercise posture displayed on the display 122 in FIG. 6E in the similar manner for a predetermined level or more, the processor 130 may display an image on the display 122 with respect to the posture following the exercise posture displayed on the display 122 in FIG. 6E.

The processor 130 may update the database about the health-related information about the user using the information about exercise of the user.

The processor 130 may determine the emotional state of the user using a camera sensor or a microphone sensor.

The processor 130 may, based on at least one of a voice of the user obtained through the microphone sensor (not shown) or a face of the user included in an image obtained through the camera sensor, determine an emotional state of the user and reproduce music corresponding to the user's emotional state through a speaker included in an audio outputter. An artificial intelligence model trained to identify a face image included in the input image and determine the emotional state may be used.

Figure 6F:
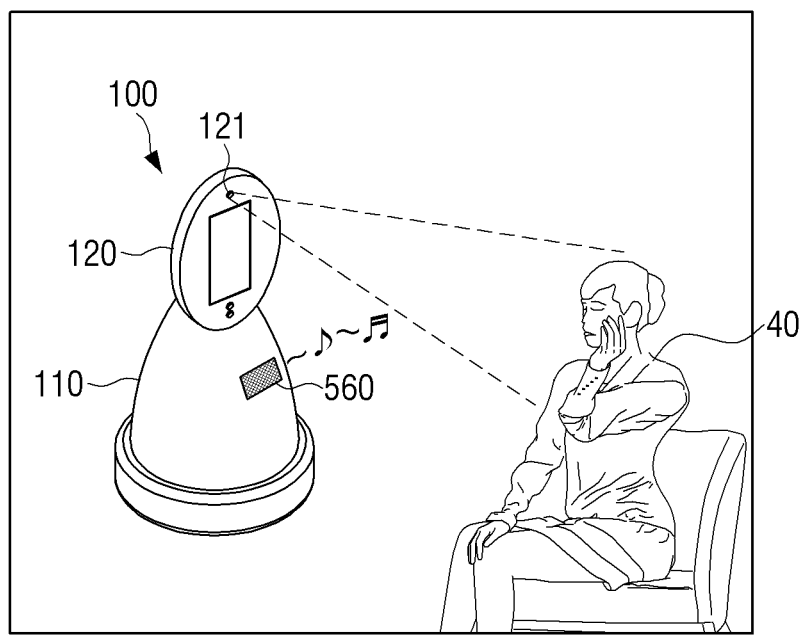
FIG. 6F is a diagram illustrating an example of an operation to obtain health-related information.

FIG. 6F is a diagram illustrating an example of determining an emotional state of a user using a camera sensor by the robot 100.

Referring to FIG. 6F, the processor 130 may control the body 110 to approach the user 40, and may capture the face of the user 40 through the camera sensor 121 to obtain the image. The processor 40 may determine that the emotional state of the user is "depressed" by analyzing the facial expression or motion of the user 40 in the obtained image.

The processor 130 may determine the emotional state of the user 40 through the voice of the user 40 received through the microphone sensor (not shown). Specifically, by performing an operation to compare the received voice tone of the user 40 with usual voice tone of the user 40 or identify whether the voice of the user 40 received through the microphone sensor (not shown) corresponds to sigh, or the like, it may be determined that the emotional state of the user is "depressed."

The emotional state of the user 40 may be determined by using information on the skin condition or the heart rate of the user 40 determined through the image obtained using the camera sensor 121, or using information on the breathing rate of the user 40 obtained through the UWB sensor.

Referring to FIG. 6F, the processor 130 may reproduce music that may console the "depressed" emotional state of the user 40 through a speaker 560 provided in the body 110. One or more suitable song may be preset for each of the plurality of emotional states, or an artificial intelligence model trained to provide information on genre or a singer of music suitable for each of the plurality of emotional states may be used.

The processor 130 may add (update) the information about the emotional state of the user 40 to the database for the health-related information of the user 40.

The processor 130 may communicate with an electronic device (not shown) of the family, lover, or acquaintance of the user 40, and may provide a video call with a family, lover or acquaintance, using the display 122, the speaker 116, the camera sensor 121, and a microphone sensor (not shown).

FIG. 7 is a diagram illustrating an example of a specific operation order of obtaining health-related information by a robot in order. FIG. 7 illustrates an example of measuring pulse rate among health-related information.

Referring to FIG. 7, when the pulse rate measurement time of the user 40 is arrived according to the predetermined schedule information in operation S710, the robot 100 may audibly provide a notification message such as "it is (pulse) measurement time" 721 through a speaker (not shown), and may find the user 40 using the body 110 and the camera sensor provided in the head 120 in operation S720.

When the user 40 authenticates the user 40 by performing the face recognition of the user 40 through the camera sensor of the head 120 in operation S730, the robot 100 may adjust the head 120 to an optimal angle to measure the pulse rate through the PPG sensor in consideration of the sitting posture of the user 40 in operation S740.

The robot 100 may measure the pulse rate as the finger of the user 40 touches the PPG sensor 123-1 in operation S750, and when measurement is completed, the angle of the head 120 may be restored to the original state and the database related to the health of the user 40 may be updated based on the measurement result in operation S760.

The robot 100 may display "personal health information" 765 including the information about a measurement result and information on a measurement result during a predetermined period of time from the present on the display of the head 120 and provide the information to the user 40. The "personal health information" 765 may include an image representing the health status of the user 40 as a level or color. However, the robot 100 may provide "personal health information" 765, only after going through authentication using face recognition, fingerprint authentication, authentication using voice recognition, etc., after measurement.

Based on receiving information on an emergent situation from an external electronic device through the communication unit of the robot 100, the processor 130 may control the body 110 to move the robot to a location corresponding to the emergent situation based on the received information about the emergent situation, and may obtain health-related information of the user existing at the corresponding location by using at least one sensor among the plurality of sensors.

The case of receiving information about the emergent situation may include cases, for example, when the information informing the occurrence of a fall of a user is received from the one or more fall detection sensors installed in a house, when receiving information informing the occurrence of a fire from the fire detection sensor device in the house, information indicating detection of the poisonous gas from the air quality sensor device in the house may be received, or the like.

The processor 130 may determine a risk of health of a user existing at a corresponding location based on the obtained health-related information, and control the communication unit to transmit the obtained health-related information to an external electronic device on the basis of the determined risk.

For example, if the user faints or has a dangerous health condition due to a fall, fire, poisonous gas, or the like, the processor 130 may notify this situation to a cell phone of a family, acquaintance through the communication unit or request an emergency rescue to an external server.

Figure 8A:
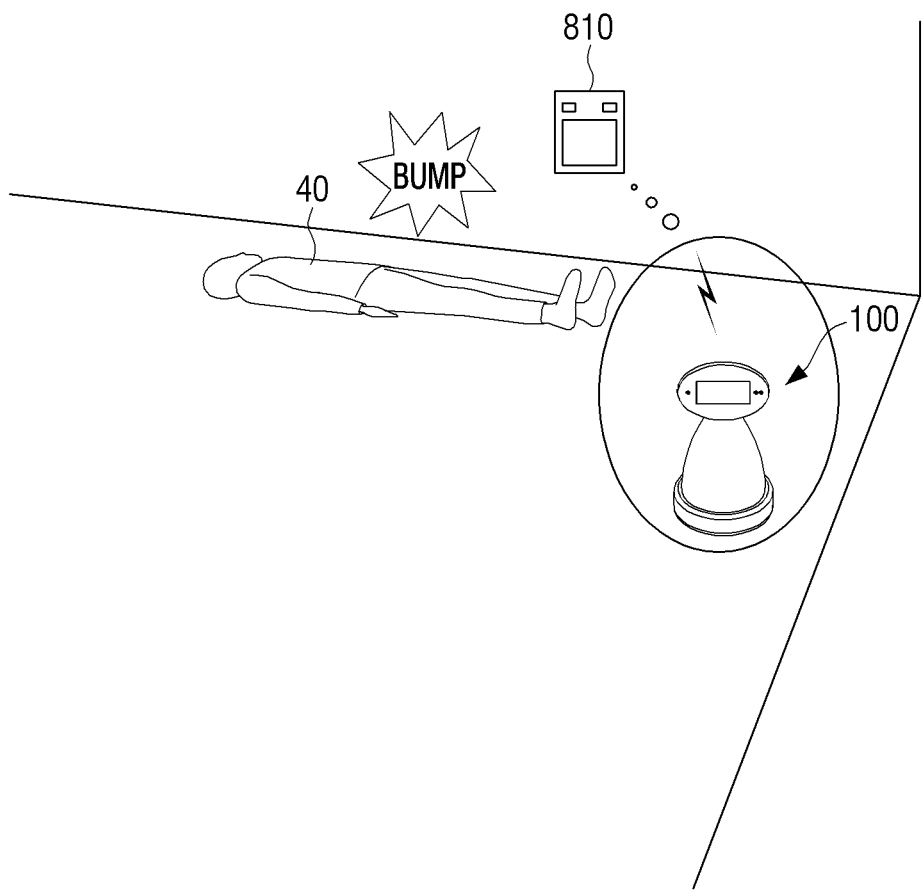
FIG. 8A is a diagram illustrating an example of operating a robot when fall is detected.
Figure 8B:
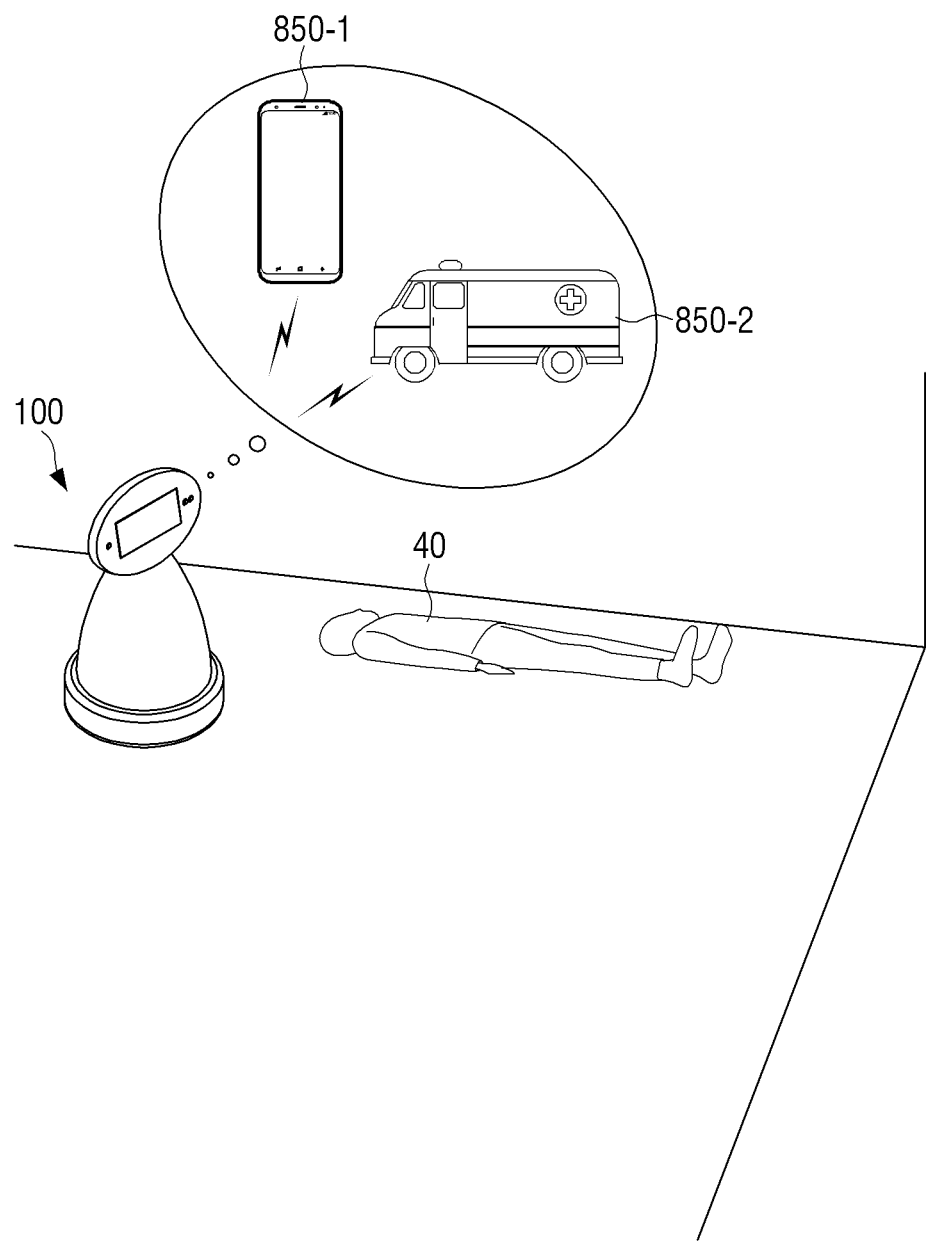
FIG. 8B is a diagram illustrating an example of operating a robot when fall is detected.

FIGS. 8A to 8B are diagrams illustrating an example in which the robot 100 operates when a fall is detected. FIGS.

8A-8B illustrate the situation in which one or more fall detection sensors are installed here and there in the house, especially, for respective rooms of a person who may fall (tumble). Here, the fall detection sensor may be a camera sensor, a depth sensor, a dynamic vision sensor (DVS), or the like, but is not limited thereto.

Referring to FIG. 8A, when fall of the user 40 is detected through one or more fall detection sensor 810 installed in the house, the robot 100 may receive, from the fall detection sensor 810, information informing occurrence of fall through the communication unit (not shown).

The processor 130 may control the body 110 to move to a location where a fall detection sensor 810 is present or a location included in the information received from a fall detection sensor 810, and may find a fallen user around a corresponding location by using one or more camera sensors.

Referring to FIG. 8B, the user 40 may obtain biometric information such as the pulse rate, blood pressure, etc. of the user 40 through one or more sensors, and may determine the risk of health of the user 40 using the obtained biometric information. Specifically, a heartbeat may be measured through a face image obtained through a camera sensor or a breathing rate may be measured through a UWB sensor. Information on the movement of the user 40 through the image obtained using the camera sensor may be obtained, and the risk of health of the user 40 may be determined by using the information.

If the degree of risk is greater than or equal to a predetermined degree (e.g., if the breathing is unstable, if there is no breathing, if the pulse is very weak or unstable, if there is no motion, or the like), the processor 130 may control the communication unit to transmit information on the user 40 to a mobile phone 850-1 and an emergency rescue 850-2 of the user 40 of family, guardian, or main doctor, or the like, of the user 40.

The processor 130 may control the communication unit to transmit the obtained biometric information of the user 40, the information on the location of the user 40, the information on the point in time of fall, the image data of the user 40 captured through the camera sensor, or the like.

The processor 130 may control the camera sensor, the microphone sensor, the speaker, the display, and the communicator to automatically perform a video call with the mobile phone 850-1 and the emergency rescue 850-2.

The processor 130 may control one or more electronic devices through the communicator (not shown) based on the obtained health-related information.

Figure 9:
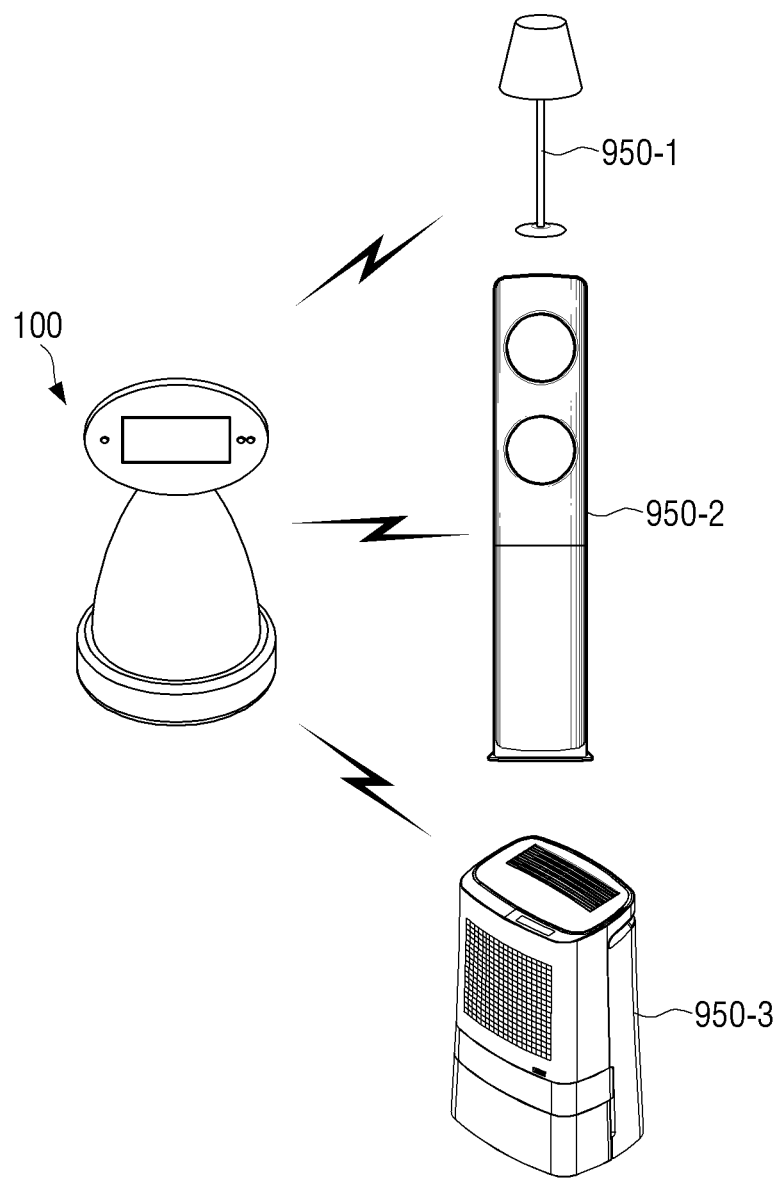
FIG. 9 is a diagram illustrating an embodiment of a robot for controlling one or more electronic devices using the obtained health-related information.

FIG. 9 is a diagram illustrating an embodiment of the robot 100 for controlling one or more electronic devices using the obtained health-related information.

Referring to FIG. 9, the robot 100 may control a lighting device 950-1, an air conditioner 950-2, an air purifier 950-3, or the like, in the house through the communicator.

For example, the robot 100 may identify a user's behavior through an image obtained using the camera sensor, and may control the lighting device 950-1. Specifically, the user may remotely control the power of the lighting device 950-1 when the lighting device 950-1 of the place where the user is located is turned on.

As another example, the robot 100 may, if the temperature detected through the temperature sensor is beyond the predetermined range from the proper indoor temperature, remotely control an air conditioner 950-2 to maintain the proper indoor temperature.

As another example, the robot 100 may remotely control the air purifier 950-3 to start operation, when it is identified that the fine dust concentration in the house is high, through the air quality sensor.

The device which the robot 100 may control through the communication unit is not limited to the above-described device, and may be other types of mobile robots or home appliances. Although not shown in FIG. 9, the robot 100 may not transmit control signals directly to the devices 950-1, 2, and 3, but may also transmit the control signals through a separate server (not shown).

The processor 130 may transmit the obtained health-related information to an external device including a server or receive health-related information from an external device.

Figure 10:
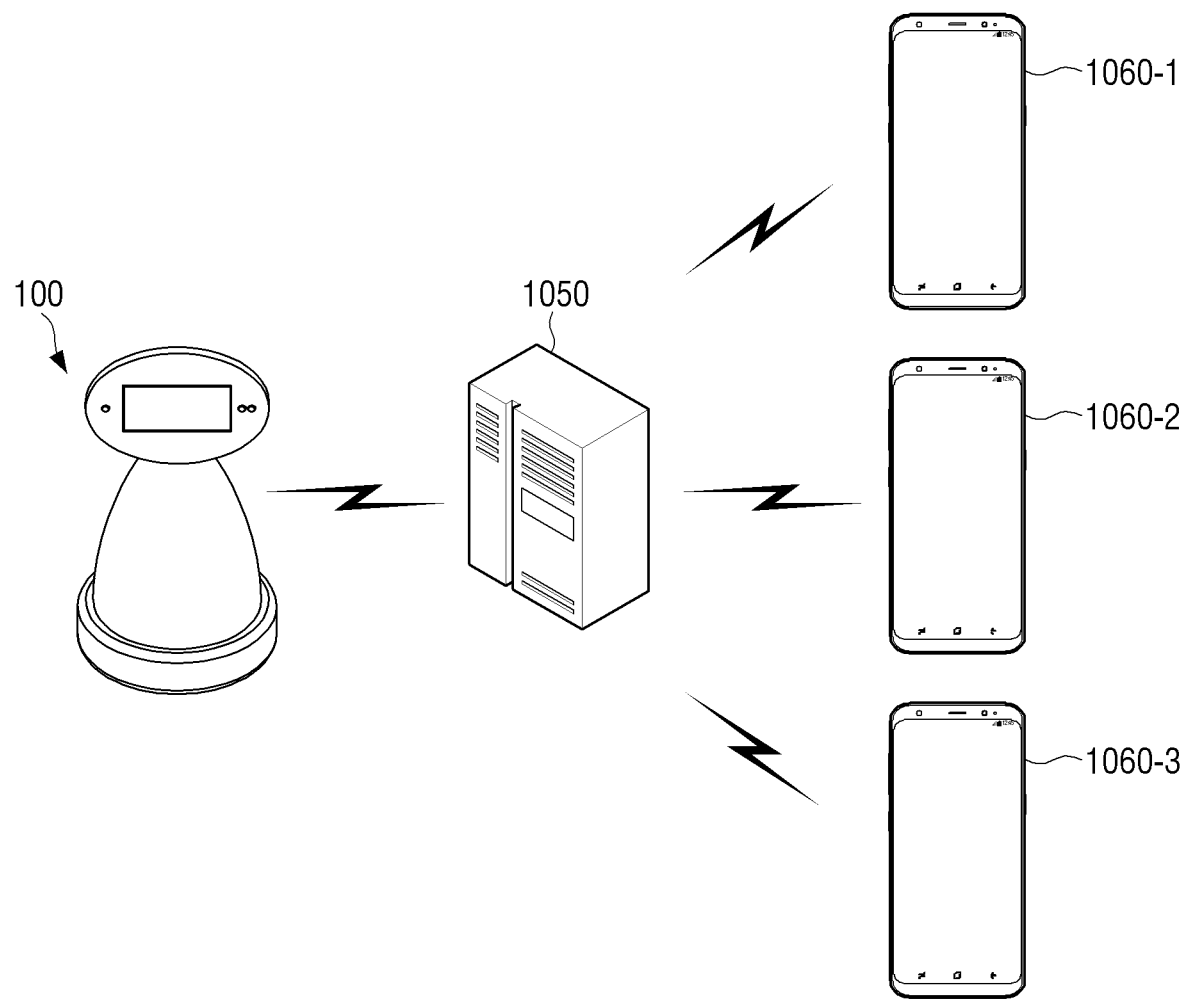
FIG. 10 is a diagram illustrating an example of providing obtained health-related information to a plurality of external devices.

FIG. 10 illustrates an example of providing obtained health-related information to a plurality of external devices or receiving health-related information from an external device.

Referring to FIG. 10, a database for health-related information of one or more users may be stored on a server 1050, and the robot 100 may transmit the health-related information to the server 1050 whenever the health-related information is obtained, and the server 1050 may provide the user's health-related information included in the database to external devices 1060-1, 1060-2, and 1060-3, such as a cellular phone of a user's family, acquaintance, nurse, main doctor, or the like.

The external devices 1060-1, 1060-2, and 1060-3 receiving the health-related information from the server 1050 may perform a separate authentication process when a command for accessing a database of a specific user is input, in order to prevent unspecified persons from easily accessing the user's health-related information stored in the database form within the server 1050.

Referring to FIG. 10, the robot 100 may receive, from the server 150, wake-up information, attention related to a body state of a user received from an electronic device and inform a user of the information through a display or an audio outputter.

The health-related information and preset schedule information obtained through the robot 100 may be linked to an application stored in one or more external devices. At this time, the external device may not only provide health-related information and preset schedule information obtained through the robot 100, but also may receive a user command to change or add schedule information to change preset schedule information. As a result, the schedule of obtaining health-related information by the robot 100 may be modified.

Figure 11:
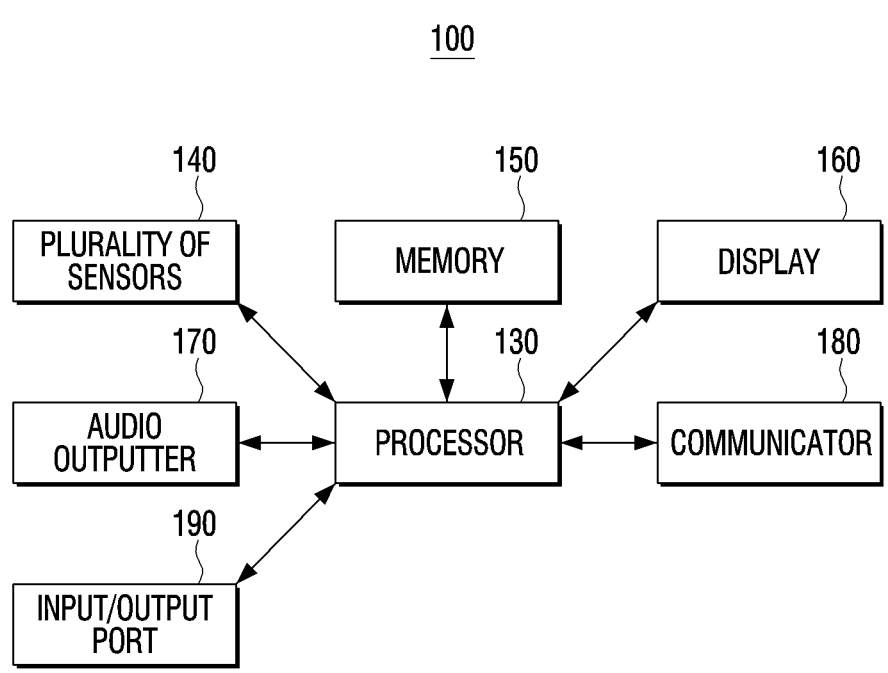
FIG. 11 is a block diagram illustrating a detailed configuration of a robot according to various embodiments of the disclosure.

FIG. 11 is a block diagram illustrating a detailed configuration of the robot 100 according to various embodiments of the disclosure.

Referring to FIG. 11, the robot 100 may include the body 110 and/or the head 120, the processor 130, and may also include a plurality of sensors 140, a memory 150, a display 160, an audio outputter 170, a communicator 180, an input/output port 190, or the like.

The plurality of sensors 140 may include various sensors for obtaining health-related information such as a photoplethysmography (PPG) sensor, a camera sensor, a microphone sensor, an ultra-wideband (UWB) sensor, an air quality sensor (fine dust sensor and/or a gas sensor), a fall detection sensor, an illuminance sensor, a temperature sensor, a body temperature detection sensor, or the like.

The plurality of sensors 140 may include sensors such as a distance sensor, a proximity sensor, a radar sensor, a GPS sensor, an acceleration sensor, and a gyro sensor, or the like.

The memory 150 may store an operating system (OS) for controlling overall operations of the elements of the robot 100 and storing instructions or data related to the elements of the robot 100.

The memory 150 may be implemented with a non-volatile memory (e.g., a hard disk, a solid state drive (SSD), a flash memory), a volatile memory, or the like.

The memory 150 may store information for controlling the body 110 and the head 120 when respective sensor disposed in the body 110 or the head 120 operates. Specifically, the information may include, when each type of sensors for obtaining different health-related information is operated, information on the distance to approach the user by the body 110, and direction and angle in which the head 120 rotates.

The memory 150 may store database on information related to health of one or more users, and the database may be updated for newly obtained health-related information.

The display 160 is configured to display one or more images according to control of the processor 130. The display 160 may be implemented as a liquid crystal display (LCD), plasma display panel (PDP), organic light emitting diodes (OLED) display, a transparent OLED (TOLED) or the like. When implemented with an LCD, in the display 160, a driving circuit (not shown), a backlight (not shown), or the like, which may be implemented as an a-si TFT, low temperature poly silicon (LTPS) TFT, organic TFT (OTFT), or the like, may be included as well.

The display 160 may include a touch sensor in which a touch panel capable of detecting a touch manipulation of the user is implemented as a touch screen form including a touch panel.

The audio outputter 170 is configured to output a specific voice according to the control of the processor 130. The audio outputter 170 may be implemented as a speaker (not shown) and/or a headphone/earphone output terminal (not shown).

The processor 130 may provide obtained information related to health visually and audibly through the display 160 and/or the audio outputter 170.

The communicator 180 is configured as a circuit and is a means to perform data communication with an external device (not shown) by wire or wirelessly. The processor 130 may perform communication with various external devices using the communicator 180.

When performing data communication with an external device in a wireless communication method, the communicator 180 may include at least one of a WiFi direct communication module, a Bluetooth module, an infrared data association (IrDA module, a near field communication (NFC) module, a Zigbee module, a cellular communication module, a 3rd generation (3G) mobile communication module, a fourth generation (4D) mobile communication module, a fourth Long Term Evolution (LTE) communication module, or a 5th generation (5G) mobile communication module.

When performing data communication with an external device by wired communication method, the communicator 180 may be connected to a coaxial cable, an optical cable, or the like, to perform local area network (LAN) and may transceive various data.

The processor 130 may obtain health-related information from various external devices through the communicator 180, or may transmit the health-related information obtained through the plurality of sensors 140 to various external devices.

Through the input/output port 190, the robot 100 may receive power from the outside or supply power to the outside. Also, through the input/output port 190, the robot 100 may receive signal/data for image/audio from the outside, or transmit data/signals for image/audio to the outside.

The input and output port 190 may be implemented as a wired port such as a high-definition multimedia interface (HDMI) port, a display port, a red-green-blue (RGB) port, a digital visual interface (DVI) port, Thunderbolt and component ports.

The input and output port 190 may be implemented with the HDMI port or the Thunderbolt, or the like, and may be implemented to transmit an image and an audio signal, but the first port for transmitting an image signal and the second port for transmitting an audio signal may be separately implemented.

The input/output port 190 may include an interface module, such as a universal serial bus (USB), and may be physically connected to an external terminal device such as a personal computer (PC) through the interface module to transmit and receive voice or image data or to transmit and receive firmware data for performing firmware upgrade.

Figure 12:
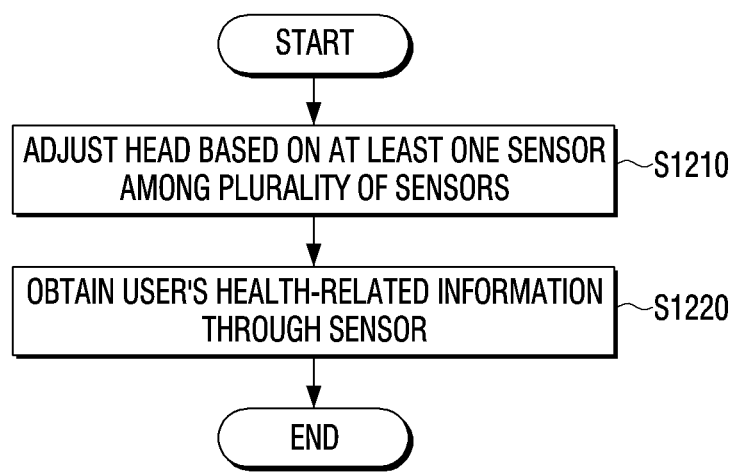
FIG. 12 is a flowchart illustrating a control method of a robot according to an embodiment of the disclosure.
Figure 13:
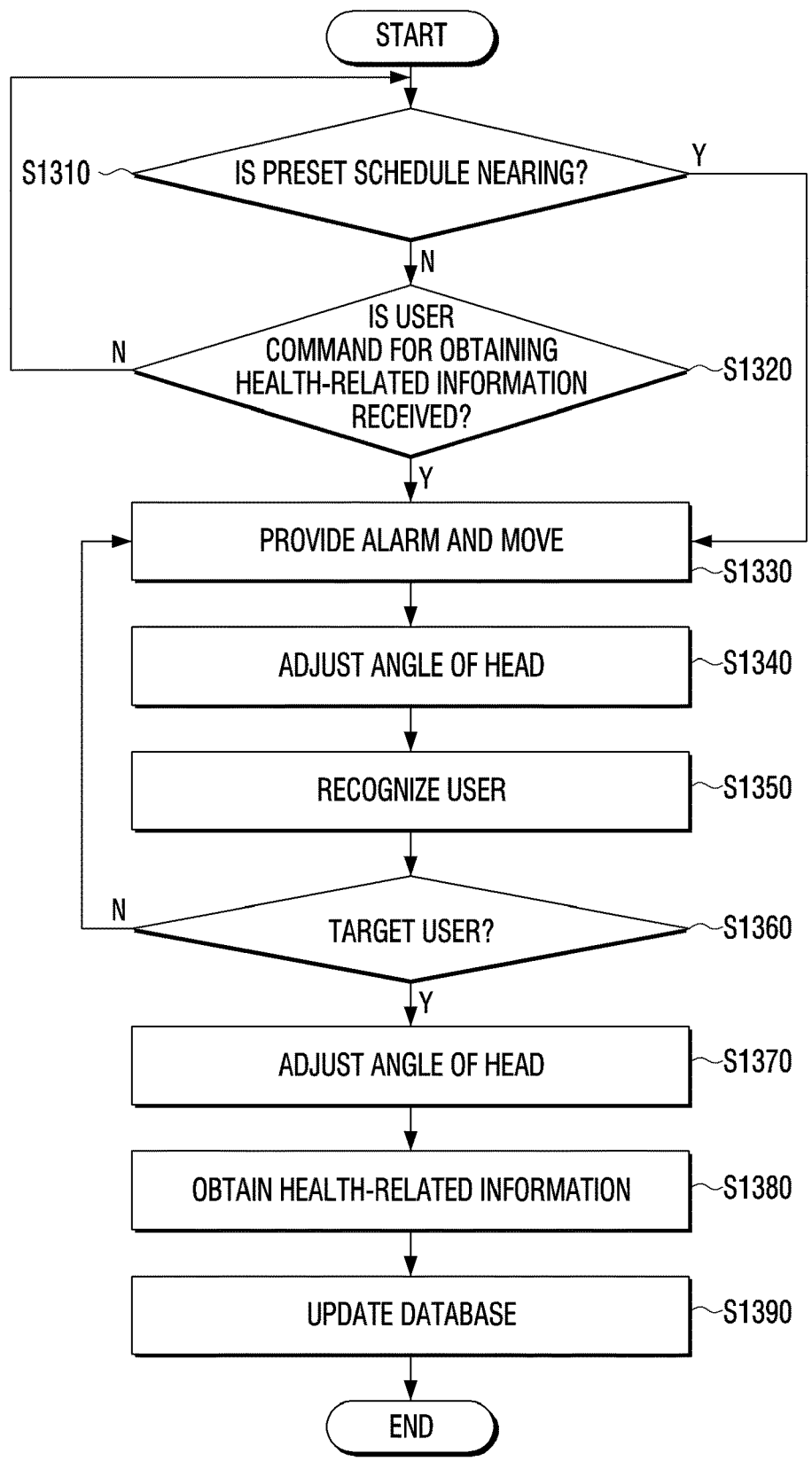
FIG. 13 illustrates an algorithm illustrating a specific example of a method of controlling a robot according to an embodiment of the disclosure.

Referring to FIGS. 12 to 14, a control method for a robot including a body with a moving means and a head that is disposed on the body and includes a plurality of sensors will be described.

FIG. 12 is a flowchart illustrating a control method of a robot according to an embodiment of the disclosure.

Referring to FIG. 12, the control method may include adjusting a head of the robot based on at least one sensor among a plurality of sensors in operation S1210. The method may include, based on a time to obtain the health-related information nearing according to preset schedule information, controlling the body so that the robot approaches a user, and adjusting the head of the robot based on the sensor corresponding to the preset schedule information. The body and the head of the robot may be controlled based on received or input user command, instead of preset schedule information.

A distance between the robot and the user may be determined to obtain health-related information based on the type of the sensor and the body may be controlled so that the robot may approach the user based on the determined distance.

A motion angle of the head may be determined based on at least one of a location of the sensor or a type of the sensor on the head and the head may be adjusted based on the determined motion angle. In this example, the head may be adjusted considering at which location and in which direction on the head, the sensor is disposed.

The user's posture may be determined based on the image obtained through the camera sensor, among the plurality of sensors and the head may be adjusted based on the determined posture.

The user's health-related information may be obtained through the sensor on the controlled head in operation S1220. The health-related information may be obtained by using a sensor for obtaining health-related information corresponding to predetermined schedule information among a plurality of sensors.

The health-related information may further include biometric information such as heart (pulse) rate, blood pressure, breathing rate, eyeball state, voice, skin condition, body temperature, stress degree, emotional state, etc., and various pieces of information necessary for health management. For example, information on the exercise of a user, information on a user's medication, information on a user's posture, information on the user's surrounding environment (e.g., air quality, lighting environment, noise, temperature), information on an accident occurrence (e.g., a fall accident of a user), and the like, may be included.

For example, based on a time for the user to take a medicine nearing according to preset schedule information, an image may be obtained by capturing the user through the camera sensor, determine whether the user takes medicine based on the obtained image, and database for the health-related information of the user may be updated based on the determined information about whether the user takes medicine.

As another example, based on an exercise time of the user nearing based on preset schedule information, an image to guide the exercise of the user may be displayed, and information about the exercise of the user may be obtained based on the image obtained through the camera sensor. In this example, another image to guide the exercise of the user may be displayed based on the obtained information about the user's motion.

The control method may include performing a process for finding a user to obtain health-related information prior to operation S1210. To be specific, people existing in a specific place may be identified by using a camera sensor, a radar sensor, a proximity sensor, a microphone sensor, or the like, and a user for obtaining health-related information may be found by controlling the body to move the robot.

In this example, authentication for a user may be performed using an image obtained through the camera sensor among the plurality of sensors. In this example, authentication may be performed for one or more users, and the authentication method may include recognition of a face using a camera, voice recognition through a microphone sensor, or fingerprint recognition through a fingerprint sensor.

After operation S1220, the database for health-related information of the authenticated user may be updated based on the obtained health-related information obtained through S1220.

FIG. 13 illustrates an algorithm illustrating a specific example of a method of controlling a robot according to an embodiment of the disclosure.

Referring to FIG. 13, when a predetermined schedule for obtaining specific health-related information nears in operation S1310-Y, the body 110 may be controlled to provide an alarm for obtaining relevant health-related information and to move to find a target user in operation S1330.

In operation S1310-N, if a user command for obtaining health-related information is received or inputted S1320-Y, even if the preset schedule is not nearing in operation S1310-N, the body may be controlled to provide an alarm for obtaining relevant information and to move to find a target user in operation S1330.

By recognizing a fact of one or more users through a head camera sensor, a target user may be found. At this time, the body may be controlled to move to a location suitable for recognizing the face of respective user and at the same time, the angle of the head may be adjusted in operation S1340. By recognizing the face of each user in operation S1350, whether the user is a target user may be determined in operation S1360.

If the user of which face is recognized is not the target user in operation S1360-N, a process of moving to another user to recognize the face of the user in operation S1330-S1340-S1350 may be repeated.

If the user of which face is recognized is the target user in operation S1360-Y, the angle of the head may be adjusted to be suitable for the sensor for obtaining the corresponding health-related information in operation S1370, and the health-related information of the target user may be obtained in operation S1380. The body may be controlled to move to a location suitable for a sensor for obtaining relevant health-related information.

By adding the obtained health-related information to the database of the user, the database of the target user may be updated in operation S1390.

The method may include, based on receiving information about an emergent situation from an external electronic device through the communicator, controlling the body so that the robot moves to a location corresponding to the emergent situation based on the received information about the emergent situation, and obtaining health-related information of a user present in the location using at least one sensor among the plurality of sensors.

The method may include determining a level of risk of health of the user present in the location based on the obtained health-related information and transmitting the obtained health-related information to an external electronic device based on the determined level of risk.

The case of receiving information about the emergent situation may include cases of, for example, when the information informing the occurrence of a fall of a user is received from the one or more fall detection sensors installed in the house, when receiving information informing the occurrence of a fire from the fire detection sensor device in the house, information indicating detection of the poisonous gas from the air quality sensor device in the house may be received, or the like.

FIG. 14 is a flowchart to describe a detailed embodiment for a control method when fall is detected through a fall detection sensor in a control method of a robot.

Referring to FIG. 14, when information on a fall is obtained from a fall sensor in operation S1410, the body may be controlled to move to a location where the fall occurs in operation S1420. The information on the fall may include at least one of a fall occurrence time point, an identification number of the fall sensor, or information on a location of the fall sensor, and may identify a location where a fall occurs by using information on the fall.

After moving to a location where fall occurs, a user who experienced fall may be found through a camera sensor attached to the head. For this, the head may be adjusted in operation S1430.

If the user who experienced fall is found, who is the user may be recognized through the camera sensor in operation S1440, and the head may be adjusted in operation S1450 to obtain the biometric information of the corresponding user in operation S1460. Specifically, the information about the pulse rate, breathing rate, or the like, of the user may be obtained through the camera sensor, the UWB sensor, or the like, and the angle of the head may be changed according to the used sensor.

In operation S1470, the risk of health of the corresponding user may be determined through the obtained biometric information in operation S1470. If the determined degree of risk is greater than or equal to a predetermined degree, the information on the determined risk degree may be transmitted to an external device such as a mobile phone or an emergency rescue of a guardian in operation S1480. In this case, an image of a corresponding user obtained through the camera sensor may be transmitted to an external device, and a video call with a corresponding user may be provided to the external device using a camera sensor, a microphone sensor, a speaker, a display, and a communication unit.

The control method of the robot as described with reference to FIGS. 12 to 14 may be implemented through the robot 100 illustrated in FIGS. 2 and 11.

The control method of the robot described in FIGS. 12 to 14 may be implemented through a system including the robot 100 and one or more external devices (not shown).

The various example embodiments described above may be implemented in a recordable medium which is readable by computer or a device similar to computer using software, hardware, or the combination of software and hardware.

By hardware implementation, the embodiments of the disclosure may be implemented using, for example, and without limitation, at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electric units for performing other functions, or the like.

In some cases, embodiments described herein may be implemented by the processor 130 itself. According to a software implementation, embodiments such as the procedures and functions described herein may be implemented with separate software modules. Each of the above-described software modules may perform one or more of the functions and operations described herein.

The computer instructions for performing the processing operations of the electronic device 100 according to the various embodiments described above may be stored in a non-transitory computer-readable medium. The computer instructions stored in this non-transitory computer-readable medium may cause the above-described specific device to perform the processing operations in the electronic device 100 according to the above-described various example embodiments when executed by the processor of the specific device.

The non-transitory computer readable medium refers to a medium that stores data semi-permanently rather than storing data for a very short time, such as a register, a cache, a memory or etc., and is readable by an apparatus. In detail, the aforementioned various applications or programs may be stored in the non-transitory computer readable medium, for example, a compact disc (CD), a digital versatile disc (DVD), a hard disc, a Blu-ray disc, a universal serial bus (USB), a memory card, a read only memory (ROM), and the like, and may be provided.

The foregoing example embodiments and advantages are merely examples and are not to be understood as limiting the disclosure. The disclosure may be readily applied to other types of devices. The description of the embodiments of the disclosure is intended to be illustrative, and not to limit the scope of the claims, and many alternatives, modifications, and variations will be apparent to those skilled in the art.

What is claimed is:

1. A robot comprising:
    a body configured to include a moving means;
    a head that is disposed on the body and includes a plurality of sensors, the plurality of sensors comprising a camera sensor; and
    a processor configured to:
        perform authentication for a user using an image obtained through the camera sensor, the obtained image including the user;
        identify at least one sensor among the plurality of sensors based on health-related information to be obtained from the user, among a plurality of pieces of health-related information;
        identify a motion angle of the head to obtain the health-related information of the user based on at least one of a location of the at least one sensor on the head, a type of the at least one sensor, or a posture of the user included in the image;
        rotate, based on the identified motion angle, the head to adjust a posture of the head at an angle suitable for the at least one sensor to obtain the health-related information;
        identify a distance information to obtain the health-related information of the user based on the type of the at least one sensor;
        control the moving means so that the robot accesses the user based on the identified distance information; and
        obtain the health-related information of the user through the at least one sensor.

2. The robot of claim 1, wherein the processor is further configured to:
    based on a time to obtain the health-related information nearing according to preset schedule information, control the body so that the robot approaches the user, and
    identify the at least one sensor based on the health-related information included in the preset schedule information.

3. The robot of claim 1,
    wherein the processor is further configured to:
    update database for the health-related information of the user based on the health-related information obtained through the at least one sensor.

4. The robot of claim 1,
    wherein the processor is further configured to:
        based on a time for the user to take a medicine according to preset schedule information, determine whether the user takes medicine based on the obtained image, and
        update database for the health-related information of the user based on whether the user takes medicine.

5. The robot of claim 1, further comprising:
    a display;
    wherein the processor is further configured to:
        based on an exercise time of the user nearing based on preset schedule information, display an image to guide exercise of the user on the display,
        obtain information about the exercise of the user based on the image, and
        display another image to guide the exercise of the user on the display based on the information about the exercise of the user.

6. The robot of claim 1, further comprising:
    a speaker,
    wherein the plurality of sensors comprise a camera sensor and a microphone sensor,
    wherein the processor is further configured to:
        based on at least one of a voice of the user obtained through the microphone sensor or a face of the user included in the obtained image, determine an emotional state of the user, and
        reproduce music corresponding to the emotional state of the user through the speaker.

7. The robot of claim 1, further comprising:
a communicator comprising a circuitry,
wherein the processor is further configured to:
based on receiving information about an emergent situation from an external electronic device through the communicator, control the body so that the robot moves to a location corresponding to the emergent situation based on the received information about the emergent situation, and
obtain health-related information of the user present in the location using the at least one sensor.

8. The robot of claim 7, wherein the processor is further configured to:
determine a level of risk of health of the user present in the location based on the obtained health-related information, and
control the communicator to transmit the obtained health-related information to an external electronic device based on the determined level of risk.

9. A control method of a robot comprising a body including a moving means and a head disposed on the body and including a plurality of sensors, the method comprising:
performing authentication for a user using an image obtained through a camera sensor included in the plurality of sensors, the obtained image including the user;
identifying at least one sensor among the plurality of sensors based on health-related information to be obtained from the user, among a plurality of pieces of health-related information;
identifying a motion angle of the head to obtain the health-related information of the user based on at least one of a location of the at least one sensor on the head, a type of the at least one sensor and a posture of the user included in the image;
rotating, based on the identified motion angle, the head to adjust a posture of the head at an angle suitable for the at least one sensor to obtain the health-related information;
identifying a distance information to obtain the health-related information of the user based on the type of the at least one sensor;
controlling the moving means so that the robot accesses the user based on the identified distance information; and
obtaining the health-related information of the user through the at least one sensor.

10. The method of claim 9, further comprising:
based on a time to obtain the health-related information nearing according to preset schedule information, controlling the body so that the robot approaches the user; and
identifying the at least one sensor based on the health-related information included in the preset schedule information.

* * * * *